United States Patent [19]

Ratcliffe et al.

[11] Patent Number: 4,459,193

[45] Date of Patent: Jul. 10, 1984

[54] DENTAL COMPOSITIONS CONTAINING CAMPHORQUINONE AND ORGANIC PEROXIDE AS CATALYST

[75] Inventors: Maurice J. Ratcliffe, Congleton; Derek J. Shaw, Knutsford, both of England

[73] Assignee: Imperial Chemical Industries PLC, London, England

[21] Appl. No.: 354,795

[22] Filed: Mar. 4, 1982

[30] Foreign Application Priority Data

Mar. 4, 1981 [GB] United Kingdom ................. 8106818

[51] Int. Cl.$^3$ ................................................ C08F 2/50
[52] U.S. Cl. ........................ 204/159.23; 204/159.15; 523/115; 523/116; 526/208; 433/228
[58] Field of Search ...................... 204/159.23, 159.15; 523/115, 116; 526/273, 208

[56] References Cited

U.S. PATENT DOCUMENTS

| | | | |
|---|---|---|---|
| 2,367,660 | 1/1945 | Agre | 204/158 |
| 3,931,678 | 1/1976 | O'Sullivan et al. | 204/159.23 |
| 4,071,424 | 1/1978 | Dart et al. | 204/159.14 |
| 4,097,994 | 7/1978 | Reaville et al. | 204/159.23 |
| 4,110,184 | 8/1978 | Dart et al. | 523/116 |
| 4,222,835 | 9/1980 | Dixon | 204/159.23 |
| 4,325,794 | 4/1982 | Hunter et al. | 204/159.23 |

FOREIGN PATENT DOCUMENTS

| | | |
|---|---|---|
| 2506650 | 8/1976 | Fed. Rep. of Germany . |
| 569974 | 6/1945 | United Kingdom . |
| 1408265 | 10/1975 | United Kingdom . |
| 2016994A | 9/1979 | United Kingdom . |
| 2018666A | 10/1979 | United Kingdom . |

OTHER PUBLICATIONS

Chemical Abst., vol. 52, No. 4, Feb. 25, 1958, col. 2566b.
Polymer Science & Technology, vol. 14, 1981, Plenum, N.Y., pp. 411–417.

Primary Examiner—Wilbert J. Briggs, Sr.
Attorney, Agent, or Firm—Cushman, Darby & Cushman

[57] ABSTRACT

A visible light cure fluid dental composition which comprises at least one polymerizable ethylenically unsaturated material, from 40% to 90% by weight of the composition of at least one particulate filler, and a catalyst which comprises at least one ketone having photosensitive catalytic action selected from fluorenone and α-diketones and their derivatives, and at least one organic peroxide, and a method for their preparation and use.

15 Claims, 11 Drawing Figures

DENTAL COMPOSITIONS CONTAINING CAMPHORQUINONE AND ORGANIC PEROXIDE AS CATALYST

This invention relates to dental compositions comprising polymerisable material and inorganic filler.

Many polymerisable materials have been used for dental applications. Examples of materials include polyurethanes, monomeric and polymeric acrylates and methacrylates, polyamides, epoxy-compounds, polystyrenes. Many applications have been envisaged such as fillings, crowns, denture base, coating, sealants and cements. In some of these applications it has been proposed to add inorganic fillers in order to confer desired pigmentation and/or strength.

Preferred polymerisable materials used in dental filling compositions include the reaction product of bisphenol A and glycidyl methacrylate, sometimes called bis-GMA as described in U.S. Pat. No. 3,066,112 and vinyl urethane prepolymer such as those described in British patent specification No. 1,352,063. These ethylenically unsaturated materials are polymerised in situ using a conventional redox (e.g. amine-peroxide) catalyst system or ultra-violet or preferably visible light catalyst system such as that described in British patent specification No. 1,408,265. The composition may contain up to about 90% by weight of an inert inorganic filler as described in for example British patent specification Nos. 1,465,897, 1,488,403, 1,498,421. U.S. Pat. Nos. 3,629,187 and 3,709,866, German Offenlegungsschrift Nos. 2419887 and 2816823 and European patent publication No. 0013491.

It is important when a tooth is being filled that the visible light cure filling material should cure (i.e. harden rapidly under exposure to visible light and that the cure should be essentially homogeneous throughout the entire volume of the filling. The dentist is able then to be assured that the filling is satisfactory and the patient can immediately after treatment use the teeth without waiting for the filling to cure.

It has now been found unexpectedly that the depth of cure of a visible light cured dental composition is increased and that cure is more homogeneous than such compositions described hitherto if the catalyst system comprises a mixture of ketone and organic peroxide.

According to the present invention a visible light cure fluid dental composition is provided which comprises at least one polymerisable ethylenically unsaturated material, from 40% to 90% by weight of the composition of at least one particulate filler, and a catalyst which comprises at least one ketone having photosensitive catalytic action selected from fluorenone and $\alpha$-diketones and their derivatives and at least one organic peroxide.

The dental compositions of the present invention may be used in many dental applications such as for example filling materials, orthodontic cements and restorative materials. The compositions may be pigmented as required in order to match the colour of a tooth and/or adjacent teeth.

The compositions of the present invention are fluid, that is paste-like and not powdery or crumbly at ambient temperatures so that in the uncured state they may be shaped in a coherent mass and maintain that shape without substantial flow. Such characteristics will enable the composition to be inserted into a cavity in or mould on a tooth in the upper jaw without deformation before cure. Accordingly in the present compositions the polymerisable material has a viscosity such that the present composition, which contains 40% (preferably 60%) to 90% by weight of particulate filler, will have the required fluid, paste-like consistency.

The composition may contain a mixture of polymerisable ethylenically unsaturated materials. If one or more of those materials is solid or semisolid, then one or more other component polymerisable materials should be liquid at ambient temperatures in order to confer on the composition a paste-like consistency. If desired all the polymerisable materials may be liquid at ambient temperatures. The viscosity of the polymerisable material and consistency of the composition may be controlled by adjusting the mixture of polymerisable materials.

The polymerisable material includes those referred to above but is preferably liquid ethylenically unsaturated material such as a vinyl urethane, for example, those described in British patent specification Nos. 1,352,063, 1,465,097, 1,498,421 and German Offenlegungsschrift No. 2419887 or the reaction product of a diol such as glycol but particularly a bisphenol with a glycidyl alkacrylate such as those described for example in U.S. Pat. Nos. 3,066,112 and 4,131,729 (the disclosures in these specifications are incorporated herein by way of reference).

A preferred reaction product of a glycidyl alkacrylate and a diol has the formula:

Preferred vinyl urethanes described in the aforesaid British patent specifications and German Offenlegungsschrift are the reaction product of a urethane prepolymer and an ester of acrylic or methacrylic acid with a hydroxy alkanol of at least 2 carbon atoms, the urethane prepolymer being the reaction product of a diisocyanate of the structure $OCN-R^1-NCO$ and a diol of the structure $HO-R^2-OH$ wherein $R^1$ is a divalent hydrocarbyl group and $R^2$ is the residue of a condensate of an alkylene oxide with an organic compound containing two phenolic or alcoholic groups.

Other suitable vinyl urethanes include those made by the reaction of alkyl and aryl, preferably alkyl, diisocyanates with hydroxy alkyl acrylates and alkacrylates such as those described in British patent specification Nos. 1,401,805, 1,428,672 and 1,430,303 (the disclosures of which are included herein by way of reference).

Liquid ethylenically unsaturated monomers (the polymers of which should be water insoluble) suitable as polymerisable materials include vinyl monomers, e.g. vinyl esters such as n-hexyl, cyclohexyl and tetrahydrofurfuryl acrylates and methacrylates. The monomers should have low toxicity and volatility.

Polyfunctional monomers are also suitable as polymerisable materials vinyl monomers, that is, monomers containing two or more vinyl groups. Suitable monomers include, for example, glycol, dimethacrylates, diallyl phthalate, and triallyl cyanurate.

A preferred polymerisable material comprises a mixture of vinyl urethane or glycidyl alkacrylate and 25% to 150% by weight of vinyl urethane or glycidyl alkacrylate of at least one polyfunctional monomer hereinbefore described.

The dental compositions of the present invention are cured by irradiating the composition with visible radiation, preferably that having a wavelength in the range 400 mμ to 500 mμ. In order that curing of the compositions may be achieved in that range, the compositions contain at least one ketone selected from fluorenone and diketone and at least one organic peroxide.

Ketones suitable for use in the compositions of the present invention also show some photosensitive catalytic action on their own without the presence of organic peroxide. Such activity of the ketone is enhanced by the addition of an organic amine as described in the aforesaid British patent specification No. 1,408,265. Accordingly the present ketones are selected from fluorenone and α-diketones and their derivatives which in admixture with a similar amount of organic amine which is capable of reducing that ketone when the latter is in an excited state, but in the absence of organic peroxide, catalyse cure of an ethylenically unsaturated material. Evidence of cure may be conveniently detected by examining the change in viscosity of a mixture of the ethylenically unsaturated material containing the ketone and organic amine each at 1% by weight based on ethylenically unsaturated material using an oscillating rheometer, samples thickness 2 mm., whilst the mixture is being irradiated with light having wavelength in the range 400 to 500 mμ. Such an examination may be carried out using the method described British Standard 5199: 1975, paragraph 6.4 provided that provision is made to allow visible light to be directed onto the mixture. Preferably the ketone has a cure time of less than 15 minutes at a radiation level of 1000 w/m² as measured at 470 mμ, bandwidth ±8 mμ, for example using a Macam Radiometer (Macam Photometrics Ltd., Edinburgh, Scotland).

Diketones have the formula:

in which the groups A, which may be the same or different, are hydrocarbyl or substituted hydrocarbyl groups and in which the groups A may be further linked together by a divalent link or by a divalent hydrocarbyl or substituted hydrocarbyl group or in which the groups A together may form a fused aromatic ring system. Preferably the groups A are the same.

The groups A may be aliphatic or aromatic. Within the scope of the term aliphatic are included cycloaliphatic groups and aliphatic groups which carry aromatic substituents, that is, aralkyl groups. Similarly within the scope of the term aromatic group are included groups which carry alkyl substituents, that is, alkaryl groups. Within the term aromatic groups are included heterocyclic groups.

The aromatic groups may be a benzenoid aromatic group, e.g. the phenyl group, or it may be a non-benzenoid cyclic group which is recognised in the art as possessing the characteristics of a benzenoid aromatic group.

The groups A, especially when aromatic may carry substituent groups other than hydrocarbyl, e.g. halogen or alkoxy. Substituents other than hydrocarbyl may result in inhibition of polymerisation of ethylenically unsaturated materials, and if the α-diketone contains such substituents it preferably is not present in the photopolymerisable composition in such a concentration as to result in substantial inhibition of polymerisation of the ethylenically unsaturated material in the composition.

The groups A may be further linked together by a direct link, or by a divalent group, e.g. a divalent hydrocarbyl group, that is, in addition to the link through the group the groups A may be further linked so as to form a cyclic ring system. For example, where the groups A are aromatic the α-diketone may have the structure     I in which Ph is a phenylene group, Y is >CH₂, or a derivative thereof wherein one or both of the hydrogen atoms are replaced by a hydrocarbyl group, and m is 0, 1 or 2. Preferably the group Y is linked to the aromatic groups in positions ortho to the group The groups A together may form a fused aromatic ring system.

In general, α-diketones are capable of being excited by radiation in the visible region of the spectrum, that is, by light having a wavelength greater than 400 mμ, e.g. in the wavelength range 400 mμ to 500 mμ. For the present invention, α-diketone should have low volatility so as to minimise odour and concentration variation. Suitable α-diketones include benzil in which both groups A are phenyl, α-diketones in which both of the groups A are fused aromatic, e.g. α-naphthil and β-naphthil, and α-diketones in which the groups A are alkaryl groups, e.g. p-tolil. As an example of a suitable α-diketone in which the groups A are non-benzenoid aromatic there may be mentioned furil, e.g. 2:2'-furil. Derivatives of the α-diketone in which the groups A carry non-hydrocarbyl groups as for example p,p'-dialkoxy benzil, e.g. p,p'-dimethoxy benzil or p,p'-dihalobenzil, e.g. p,p'-dichlorobenzil, or p-nitrobenzil may be incorporated.

The groups A may be linked together by a direct link or by a divalent hydrocarbyl group to form a cyclic ring system. For example, where the groups A are aliphatic the α-diketone may be camphorquinone.

An example of an αdiketone having the structure I is phenanthraquinone in which the aromatic groups A being linked by a direct link ortho to the group Suitable derivatives include 2-bromo-, 2-nitro-, 4-nitro-, 3-chloro-, 2,7-dinitro-, 1-methyl-7-isopropyl phenanthraquinone.

The α-diketone may be acenaphthene quinone in which the groups A together form a fused aromatic ring system.

The present ketone may also be fluorenone and its derivatives such as for example lower alkyl (Cl-6), halo, nitro, carboxylic acid and esters thereof, particularly in the 2- and 4-positions.

The ketone may, for example, be present in the composition in a concentration in the range 0.01% to 2% by weight of the polymerisable material in the composition although concentrations outside this range may be used if desired. Suitably the ketone is present in a concentration of 0.1% to 1% and more preferably 0.5% to 1% by weight of the ethylenically unsaturated material in composition. The ketone should be soluble in the polymerisable material and the above concentrations refer to solution concentration.

The organic peroxides suitable for use in the present composition include those having the formula

R—O—O—R in which the groups R which may be the same or different, are hydrogen, alkyl, aryl, or acyl groups, no more than one of the groups R being hydrogen. The term acyl means groups having the formula $R^3$—CO— in which $R^3$ is an alkyl, aryl, alkyloxy or aryloxy group. The terms alkyl and aryl have the definitions given hereinbefore for the groups A and include substituted alkyl and aryl.

Examples of organic peroxide suitable for use in the composition of the present invention include diacetyl peroxide, dibenzoyl peroxide, ditertiary butyl peroxide, dilauroyl peroxide, tertiary butyl perbenzoate, ditertiary butyl cyclohexyl perdicarbonate.

The organic peroxide may be, for example, present in the composition in the range 0.1% to 20% by weight of the polymerisable material in the composition although concentration outside this range may be used if desired.

The reactivity of a peroxide is often measured in terms of a ten hour half life temperature, i.e. within ten hours at that temperature half of the oxygen has been made available. The peroxides in the present compositions preferably have ten hour half life temperatures of less than 150° C., more preferably less than 100° C.

The rate at which the composition of the invention cures under the influence of visible light can be increased by incorporation into the composition of reducing agent which is capable of reducing the ketone when the latter is in an excited state. Such reducing agents are described, for example, in German Offenlegungsschrift No. 2251048 and are preferably organic amines having the formula $R^4{}_3N$ where the groups $R^4$, which may be the same or different, are hydrogen atoms, hydrocarbyl groups, substituted hydrocarbyl groups or groups in which two units $R^4$ together with the nitrogen atom form a cyclic ring system, no more than two of the units $R^4$ being hydrogen atoms and where $R^4$ is attached directly to an aromatic group $R^4$, at least one of the other units $R^4$ has a group attached to the nitrogen atom. The reducing agent is preferably present in the composition in concentration in the range 0.01% to 2% by weight of the polymerisable material although concentrations outside this range may be used if desired. However, as hereinbefore described, an advantage of the present compositions is that they can be used by a dentist from a single container; the presence of a reducing agent together with an organic peroxide can lead to premature, non-visible-light initiated curing so reducing the shelf life of the composition. However in preferred compositions, a reducing agent is included in combination with a suitable organic peroxide in order to provide improved depth of cure with acceptable shelf life.

As stated hereinbefore, the present composition contains 40% to 90% by weight of a particulate filler. It is preferred that at least 50% of the particles should have a maximum dimension of not greater than 500 microns. By this is meant that the maximum dimension of the particles in any direction should not be greater than 500 microns. Thus, where the filler is in the form of spheres at least 50% of the spheres should have a diameter of not greater than 500 microns. Where the filler is in the form of fibres at least 50% of the fibres should have a length of not greater than 500 microns. Preferably substantially all of the particles in the filler have a maximum dimension of not greater than 500 microns.

The preferred maximum dimension of the particles in the filler is determined by the shape of the filler. Thus, where the filler is in the form of fibres the maximum dimension of the fibres is preferably not greater than 100 microns. On the other hand, where the filler is in the form of spheres, platelets or is irregularly shaped the maximum dimension of the particles in the filler is preferably not greater than 300 microns and is more preferably in the range 1 to 100 microns.

In order that a hard dental filling may be produced by curing of the composition it is desirable that the particles of filler have a Knoop hardness of at least 100. In general, the greater the hardness of particles of filler in the composition the greater the hardness of the dental filling produced by curing of the composition and for this reason it is preferred that Knoop hardness of the filler be at least 300, and more preferably at least 500. In general, the required hardness, and in particular the preferred hardness, is possessed by inorganic fillers.

The filler may, for example, be in the form of spheres, platelets, fibres. whiskers or it may be irregularly shaped. Suitable fillers include, for example, apatite, soda glass, quartz, silica gel, borosilicate glass, synthetic sapphire (alumina) and radio opaque fillers, e.g. barium and strontium oxide glasses.

Mixing of the components may be effected by stirring together the polymerisable material and filler. However, as the polymerisable material may be viscous and thus difficult to stir with the filler so as to achieve adequate mixing, the polymerisable material may conveniently be diluted with a suitable diluent so as to reduce the viscosity thus enabling adequate mixing of the filler to be more readily achieved. When mixing has been effected the diluent may be removed, e.g. by evaporation.

In order that a dental filling may be produced in which the filler adheres particularly well to the cured polymerisable material in the filling it is much preferred that the filler be treated with a coupling agent which is capable of reacting with both the filler and the polymerisable material before mixing of the filler and polymerisable material is effected. The coupling agent should have the effect of increasing the strength of the bond between the filler and the cured polymerisable material in the filling.

Suitable coupling agents for use with glass include silanes, e.g. γ-methacryloxypropyltrimethoxysilane, γ-aminopropyltriethoxysilane and γ-glycidoxypropyltrimethoxysilane.

The filler component of the present composition may comprise a mixture of fillers in order to provide a dental filling or artificial tooth having an optimum selection of physical properties for example compression strength, wear resistance. To this end, a preferred filler mixture comprises 5% to 55%, preferably 5% to 25%, of at least one filler having a mean size particle of less than 0.5 μm in the longest dimension, and the remainder of the filler having a mean size particle of more than 0.5 μm in the longest dimension. The above percentages are volume fractions of that filler in that filler and polymerisable material mixture.

The dental composition of the present invention is preferably packed in single small containers (e.g. 10 g. capacity) so as to facilitate handling in the surgery and reduce the risk of inadvertent curing by, for example, stray light However, where the catalyst contains an amine, the present composition may if desired be packed in two containers, one containing peroxide and the other the amine, together with such other components of the mixture such that when the contents of the two containers are mixed, e.g. in a dentist surgery, the present composition is produced; nevertheless packaging in a single container is preferred.

For cosmetic purposes the present composition may have a stained, coloured or natural tooth appearance and hence the present composition may include small quantities of pigments, opalescent agents and the like. The composition may also include small quantities of other materials such as anti-oxidants and stabilisers provided that they do not substantially affect cure.

It is preferred that the surface of the tooth be cleaned before application of the composition. The tooth may be so cleaned by for example grinding with a rotating wheel or brush or by etching using for example aqueous phosphoric acid. For complex cavities, etching and bevelling of enamel margins will improve retention and anatomic form of the composite restoration. The dental composition may be applied to the tooth, e.g. as a filling to a cavity in the tooth, and the polymerisable material is then polymerised so that the composition is formed into a hard material. When used as a dental filling material it is preferred that a cavity liner is first applied. The liner may be any normally used in the composite filling art such as polycarboxylate and calcium hydroxide aqueous slurry cements. Suitable lining cements are described in Journal of Dentistry, Vol. 6 No. 2.,1979, pages 117–125. In general it is preferred to avoid liners such as zinc oxide—eugenol liners which may interfere with the curing of the composite.

Because the photosensitive catalyst renders the polymerisable material and monomer sensitive to light in the 400 mμ to 500 mμ visible range, that part of the preparation of the present composition in which photosensitive catalyst is added and subsequent manipulation e.g. filling of containers should be carried out in the substantial absence of light in that range. Most conveniently, the preparation can be carried out using light outside that range for example under that emitted by sodium vapour electric discharge lamps.

The invention is illustrated with reference to the following Examples:

In the Examples the following test procedures were used:

Cure time was determined according to British Standard 5199:1975 (Specification for Resin-based dental filling materials), paragraph 6.4. The curing was effected by exposing the sample under test to the end of optic light guide length 11 cm. diameter 7 mm. Intensity was measured using a Macam Radiometer at 470 mμ bandwidth ±8 mμ.

The light source was a tungsten halogen lamp 12 volt, 50 watts (Thorn Electrical) with tuned reflector and a dichroic filter to eliminate UV radiation.

Knoop hardness Number (KHN) at varying depths of cure was determined by measuring Knoop hardness along the length of a composition sample in a mould which had been irradiated at one end by the above light source. A metal mould 10 mm long was provided having a flat surface and a groove 10 mm long, 3 mm wide and 1.5 mm deep along that surface. The groove was filled with composition; Mylar film and then a metal plate were placed and clamped on top of of the composition. Excess composition was removed from the open end of the groove. The composite was then irradiated for a predetermined time using the above light source with the end of the optic light guide not quite touching the composition. After irradiation the composition was post-cured at 37° C. The metal plate and Mylar film were then removed. The output from the light source was standardised for each determination to 900 w/m². Knoop Hardness Number (KHN) was determined by using a Zwick Hardness tester fitted with a Knoop Indentor, a 100 g load and a X40 lens, at 0.25 mm intervals along the length of the cured sample (i.e. depth) in the groove. KHN is the applied load divided by the projected area of indentation. The results are expressed graphically as KHN vs depth.

EXAMPLE 1

Condensate (35.2 g. 0.1 mole) obtained by reacting 2,2-bis-(4-hydroxyphenyl)propane and propylene oxide in a molar ratio of 1:2 (oxypropylated Bisphenol A) was dissolved in approximately 100 g. of methylene dichloride and the resulting solution was added dropwise to a solution of 33.6 g (0.2 mole) of hexamethylene diisocyanate in 100 g of methylene dichloride under an atmosphere of nitrogen gas. 4 drops of dibutyl tin dilaurate (available as "Mellite"12, "Mellite" is a registered trade mark) were added as catalyst. The mixture was stirred under nitrogen for 1 hour after which it was heated under reflux conditions for 9 hours. The mixture was then cooled and a solution of 29 g (0.2 mole) of hydroxypropyl methacrylate in 100 g of methylene dichloride was added after which the mixture was heated under reflux conditions for 3 hours. The hydroxypropyl ester comprised isomers in weight ratio 2-hydroxypropyl 2.6 parts to 1-methyl-2-hydroxyethyl (1 part). To the mixture of vinyl urethane and methylene chloride was added triethylene glycol dimethacrylate sufficient to produce polymerisable material containing 50% by weight vinyl urethane and 50% by weight of triethylene glycol dimethacrylate. The methylene chloride was removed by distillation.

Catalyst mixture comprising camphorquinone, organic peroxide and dimethylaminoethyl methacrylate as stated was prepared by dissolving the components in methylene chloride. The solution was added to the polymerisable material; this and subsequent steps being carried out under sodium discharge light.

The camphorquinone level was 0.3%, peroxide was 5% and dimethylaminoethyl methacrylate was 0.4% by weight based on polymerisable material.

Filler was added to the preceding material to produce a final composition containing 83% by weight of filler (barium aluminium silicate Raysorb T-3000 coated with silane A-174, Union Carbide Corporation). The final fluid composition was then produced by removing the remaining methylene chloride using a twin roll mill operating at ambient temperature under reduced pressure. The compositions were evaluated for KHN vs Depth of cure and the results are shown in the following FIGS. 1 to 6:

| FIG. | α-diketone | Peroxide | Amine | Cure time (s) | Post cure time (hr) |
|---|---|---|---|---|---|
| 1 | CQ | dilauroyl peroxide | — | 30 | 72 |
| 2 | CQ | dilauroyl peroxide | DMAEM | 30 | 48 |
| 3 | CQ | dibenzoyl peroxide* | — | 30 | 72 |
| 4 | CQ | di-tert butyl perbenzoate | DMAEM | 30 | 48 |
| 5 | CQ | di-tert butyl cyclohexyl perdicarbonate | — | 30 | 72 |
| 6** | CQ | — | DMAEM | various | 24 |

CQ = camphorquinone
DMAEM = dimethylaminoethyl methacrylate
*contains 250 ppm (on peroxide) Topanol OC (Imperial Chemical Industries Limited) 4-methyl-2,6-ditertiary-butyl phenol
**for comparison purposes.

The results show that the depth of cure of all compositions according to the present invention as represented by FIGS. 1 to 5 is greater and more homogeneous than that for a similar irradiation time of a composition containing no peroxide.

EXAMPLE 2

A series of compositions were prepared by the method described in Example 1 to show the effect on cure time of variation in the catalyst composition. The catalyst composition and cure time results are presented in the following table in which component concentrations are expressed as % by weight on polymerisable material. Measurement of cure time using the method hereinbefore described provides a guide to rate and quality of cure.

| Peroxide | | | | | |
|---|---|---|---|---|---|
| Formula | % | 10-hour half life temp. (°C.) | α-diketone % | DMAEM % | Cure time (s) |
| — | — | — | CQ 1.0 | — | 55* |
| — | — | — | — | — | no cure* |
| — | — | — | CQ 1.0 | 0.4 | 17* |
| dibenzoyl | 2.7 | 72 | — | — | no cure* |
| dibenzoyl | 0.4 | 72 | CQ 0.3 | — | 20 |
| dibenzoyl | 2.7 | 72 | CQ 0.5 | — | 15 |
| dibenzoyl | 2.7 | 72 | CQ 1.0 | — | 15 |
| dibenzoyl | 2.7 | 72 | CQ 1.0 | 0.05 | 10 |
| dibenzoyl | 2.7 | 72 | CQ 1.0 | 0.4 | 5 |
| dilauroyl | 2.7 | 63 | CQ 1.0 | — | 15 |
| dilauroyl | 5 | 63 | CQ 1.0 | 0.2 | 10 |
| tertiary butyl perbenzoate | 2.4 | 97 | CQ 1.0 | — | 25 |
| tertiary butyl perbenzoate | 2.4 | 97 | CQ 1.0 | 0.2 | 7 |
| di-tertiary butyl cyclohexyl perdicarbonate | 2.4 | 44 | CQ 1.0 | — | 15 |
| dibenzoyl | 2.7 | 72 | BZ 1.0 | 0.4 | 70 |
| — | — | — | BZ 1.0 | — | 300* |
| dibenzoyl | 5 | 72 | AC 1.0 | 0.4 | 85 |
| — | — | — | AC 1.0 | — | 170* |
| di-tertiary butyl | 2.4 | 126 | CQ 1.0 | — | 40 |
| di-tertiary butyl | 2.4 | 126 | CQ 1.0 | 0.4 | 20 |

*outside the scope of the present invention for comparison purposes only.
CQ = camphorquinone
BZ = benzil
AC = acenaphthequinone
DMAEM = dimethylaminoethyl methacrylate The results given in the table show that the cure time of compositions increase in the following order:
Peroxide alone > diketone + peroxide > diketone + peroxide + amine and
Diketone alone > diketone + peroxide.

EXAMPLE 3

A mixture of triethylene glycol dimethacrylate (TEGDM) and Bis GMA ("Nupol" 46-4005 Freeman Chemicals Corporation, Port Washington, Wis., U.S.A.) in weight ratio 1:1 was prepared in methylene chloride. Two samples of each mixture were taken; to one sample, camphorquinone was added; to the other sample Michler's ketone was added; both additions were at 1% by total weight of TEGDM and Bis-GMA. A slurry of filler in methylene chloride was prepared to which was added dibenzoyl peroxide (containing 250 ppm "Topanol"OC); the methylene chloride was removed. Portions of the above treated filler were added to each sample, the filler content being 83% by weight of composition (excluding methylene chloride) and peroxide content being 5% by total weight of TEGDM and Bis-GMA.

The resulting mixtures were each milled on a two-roll mill under reduced pressure to remove methylene chloride.

The composition containing Micheler's ketone and dibenzoyl peroxide cured on standing; the composition containing camphorquinone and dibenzoyl peroxide cured only after irradiation with the visible light for 10 seconds.

EXAMPLE 4

A mixture of triethylene glycol dimethacrylate (TEGDM) and "Atlac" 580E (Atlas Chemical Industries NV, Kortenberg, Belgium, containing 250 ppm "Topanol" OC) unsaturated polyester resin in weight ratio 1:1 was prepared in methylene chloride. Camphorquinone was added at a level of 1% by total weight of TEGDM and "Atlac"580E. A slurry of filler in methylene chloride was prepared to which was added dibenzoyl peroxide; the methylene chloride was then removed. A portion of the so-prepared filler was added to the mixture, the filler content being 83% by weight of the mixture (excluding methylene chloride) and the peroxide content being 5% by total weight of TEGDM and Bis-GMA. The resulting mixture was milled on a two-roll mill under reduced pressure to remove methylene chloride. The resultant composition had a visible light cure time of 37 seconds.

A similar composition in which methyl methacrylate replaced TEGDM had a visible light cure time of 90 seconds.

EXAMPLE 5

The procedure of Example 1 was repeated to examine variation in depth of cure at different irradiation times of composites containing the same weight concentrations of DMAEM and benzoyl peroxide (percentages below are percent by weight of polymerisable material).

Figure 1:
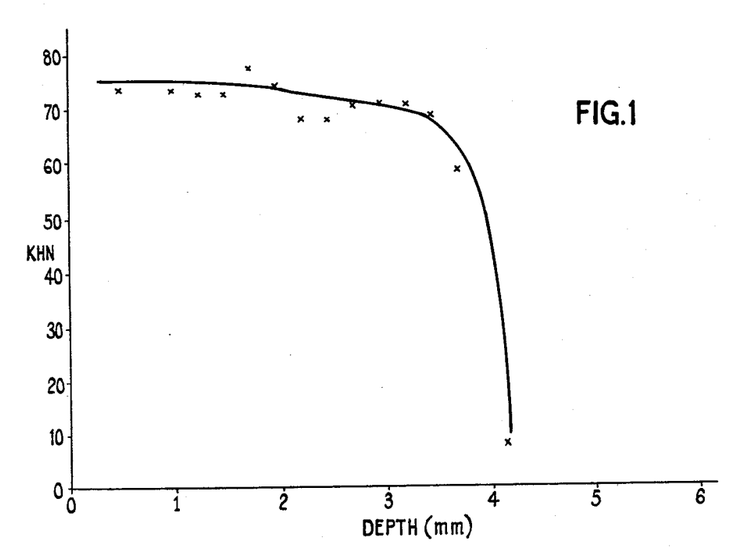
Figure 2:
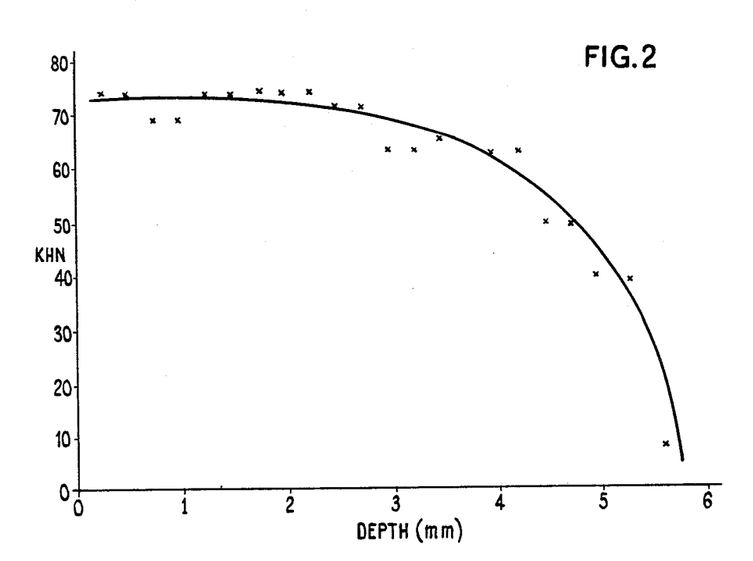
Figure 3:
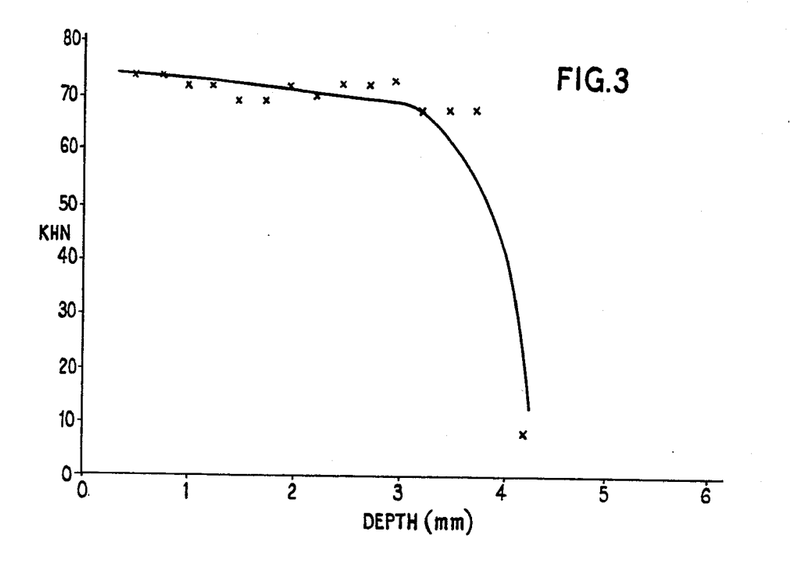
Figure 4:
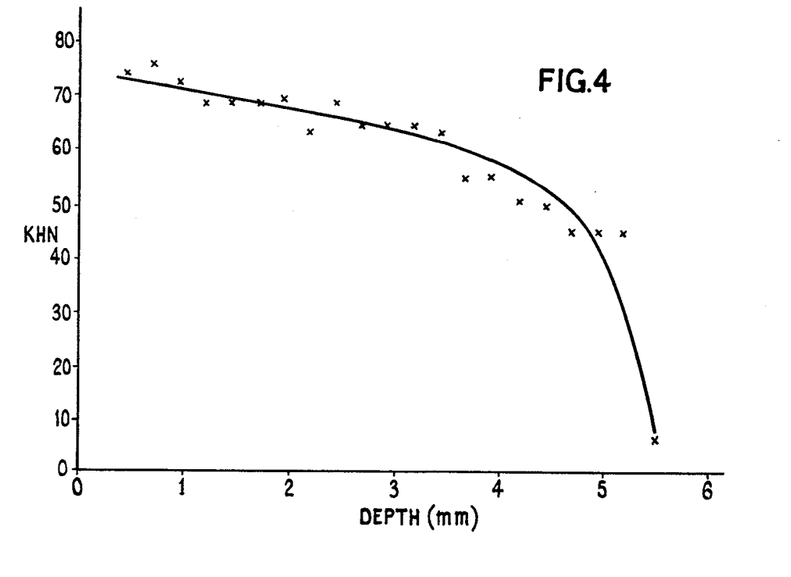
Figure 5:
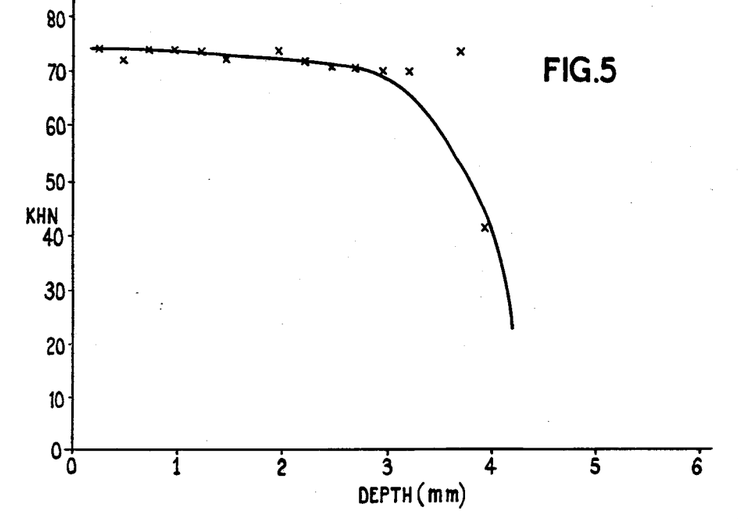
Figure 6:
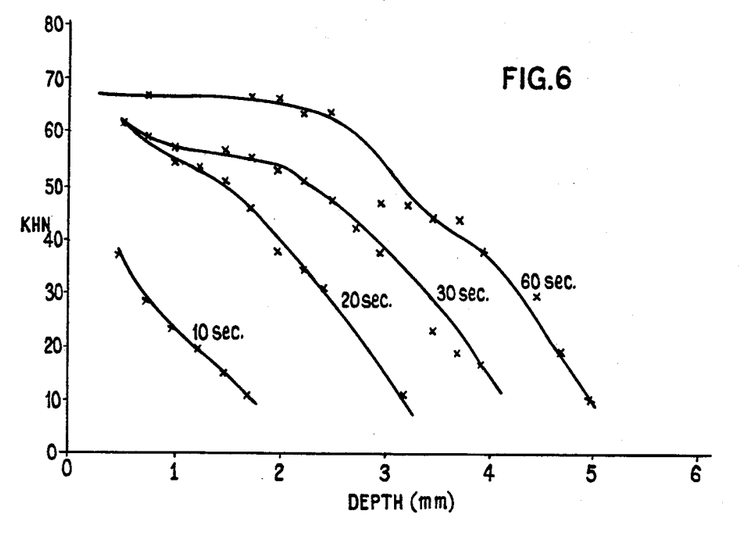
Figure 7:
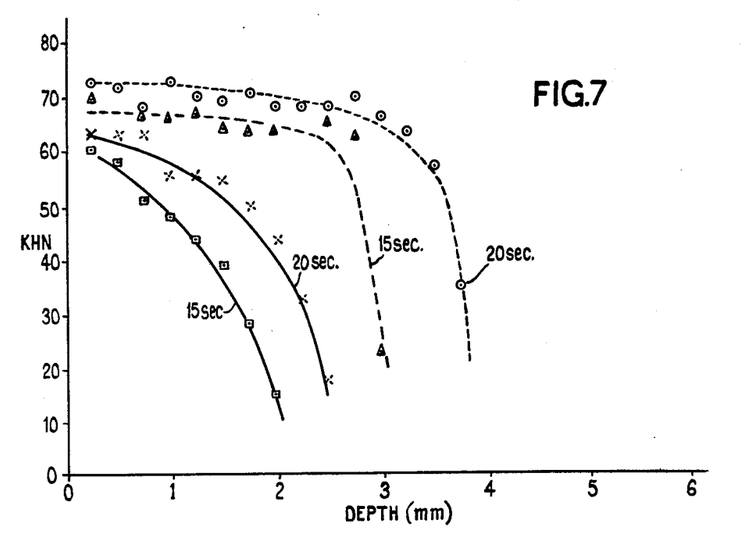

FIG. 7 presents the variation of depth of cure of compositions containing camphorquinone (1%), DMAEM (1%) shown as continuous lines and camphorquinone (1%), benzoyl peroxide (1%) shown as dashed lines, both for two irradiation times, i.e. 15 seconds and 20 seconds.

Figure 8:
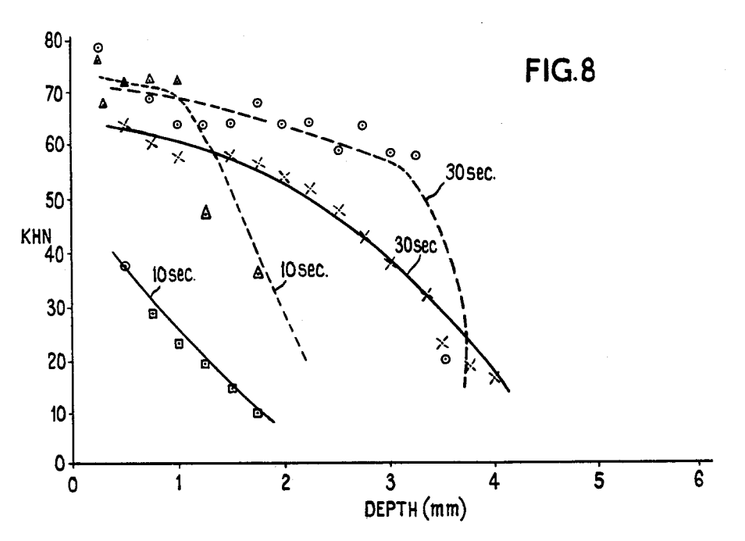

FIG. 8 presents the variation of depth of cure of compositions containing camphorquinone (0.3%) DMAEM (0.4%) shown as continuous lines and camphorquinone (0.3%) and benzoyl peroxide (0.4%) shown as dashed lines, both for two irradiation times i.e. 10 seconds and 30 seconds.

The results presented in both figures show that the $\alpha$-diketone-peroxide system of the present invention is associated with faster cure and increased depth of cure.

EXAMPLE 6

Three compositions (a, b and c) were prepared by the procedure of Example 1 except that the $\alpha$-diketone, peroxide and any amine were as follows:

(a)

Camphorquinone 1%
Tertiary butyl hydroperoxide 1%

(b)

Camphorquinone 1%
Tertiary butyl hydroperoxide 1%
DMAEM 0.2%

(c)

Camphorquinone 1%
Tertiary butyl hydroperoxide 2.5%
DMAEM 0.2%

Cure times as measured on the rheometer described hereinbefore were:
 (a) 30 seconds
 (b) 15 seconds
 (c) 15 seconds
compared with that for camphorquinone alone 55 seconds and camphorquinone/DMAEM 17 seconds in Example 2 above.

EXAMPLE 7

Two compositions (a and b) were prepared by the procedure of Example 1 except that the composition also contained 0.5% by weight of the composition of 'Aerosil' R 972(Degussa, W.Germany) and that the catalyst content was as follows:

(a)

Camphorquinone 0.3%
DMAEM 0.4%

(b)

Camphorquinone 0.3%
DMAEM 0.3%
t-butyl perbenzoate 1.5% in which percentages of catalyst component are based on polymerisable material.

Figure 9:
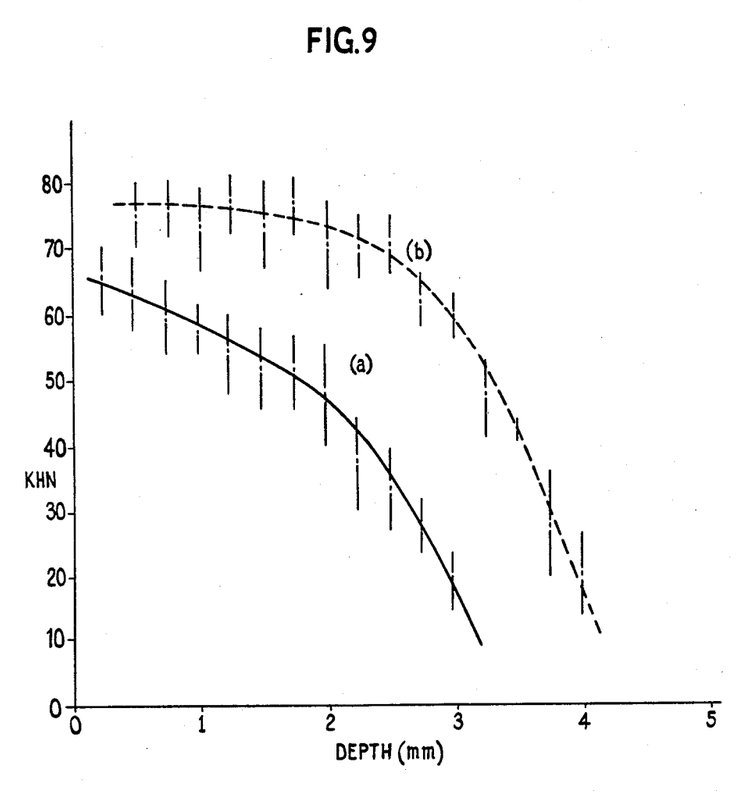

FIG. 9 presents the variation of depth of cure of the compositions (a as a continuous line, b as a dashed line) for irradiation times of (a) 20 seconds and (b) 15 seconds. The results show that the depth of cure and hardness associated with the catalyst of the present invention is greater than that for $\alpha$-diketone organic amine system.

EXAMPLE 8

Two compositions (a and b) were prepared by the procedure of Example 1 except that the catalyst content was as follows:

(a)

Fluorenone 0.25%
DMAEM 0.5%

(b)

Fluorenone 0.25%
DMAEM 0.5%
t-butyl perbenzoate 2.5% in which percentages of catalyst component are based on polymerisable material.

Figure 10:
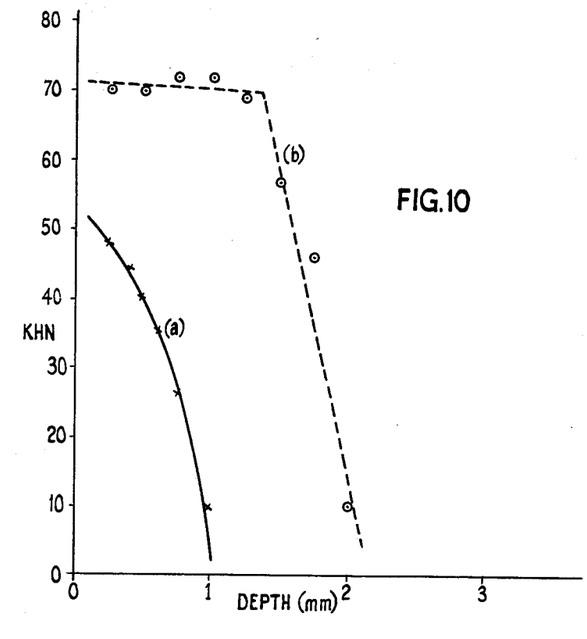

FIG. 10 presents the variation of depth of cure of the composition (a as a continuous line, b as a dashed line) after irradiation for 60 seconds using a light intensity of 1000 watts/$m^2$ measured at 470 m$\mu$. The results show that depth of cure and hardness of the present compositions is superior to those having a catalyst system of fluorenone and organic alone.

EXAMPLE 9

Figure 11:
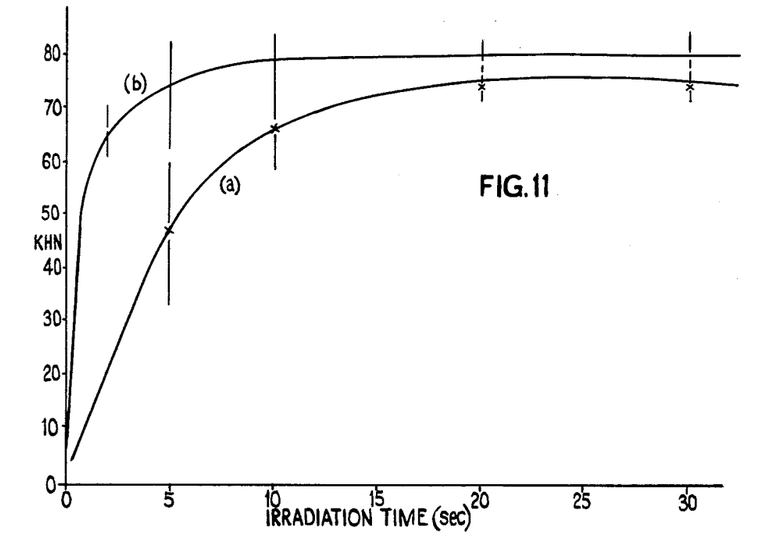

The variation of surface hardness of compositions of Example 7 was investigated over a range of cure times using a light source of intensity 970 watts/$m^2$ measured at 470 m$\mu$. The surface hardness was measured on samples after ageing in water at 37° C. for 24 hours after irradiation (seconds). The results are presented in FIG. 11 from which it is shown that the composition (b) according to the present invention attains maximum surface hardness at shorter irradiation times than composition (a) having an $\alpha$-diketone and organic amine catalyst system.

EXAMPLE 10

Mechanical properties of two compositions (a and b) prepared by the procedure of Example 1 were determined at varying times from curing. Curing was effected by irradiation for (a) 20 seconds and (b) 15 seconds using a light intensity of 1000 watts/$m^2$ measured at 470 m$\mu$.

(a)

Camphorquinone 0.3%
DMAEM 0.4%

(b)

Camphorquinone 0.3%
DMAEM 0.3%
t-butyl perbenzoate 1.5% in which the percentages of catalyst component are based on polymerisable material.

The values of mechanical properties ½ hour, 1 hour and 24 hours after curing are presented in the following table:

|  |  | (a) | (b) |
|---|---|---|---|
| Compressive | ½ hour | 26.1 ± 4.27 | 279.4 ± 7.73 |
| Strength | 1 hour | 270.0 ± 8.73 | 310.1 ± 9.24 |
| (N/mm²) | 24 hours | 308.2 ± 7.41 | 317.8 ± 6.08 |
| Diametral | ½ hour | 38.4 ± 2.06 | 51.6 ± 0.63 |
| Tensile | 1 hour | 43.3 ± 3.87 | 55.5 ± 1.52 |
| Strength |  |  |  |
| (N/mm²) | 24 hours | 52.9 ± 3.97 | 57.9 ± 1.10 |
| Flexural | ½ hour | 108.2 ± 6.48 | 144.8 ± 10.60 |
| Strength | 1 hour | 119.3 ± 7.76 | 161.8 ± 12.16 |
| (N/mm²) | 24 hours | 152.6 ± 7.63 | 154.0 ± 13.13 |
| Flexural | ½ hour | 9.46 ± 0.63 | 15.51 ± 1.28 |
| Modulus | 1 hour | 12.27 ± 0.89 | 16.01 ± 0.54 |
| (GPa) | 24 hours | 13.71 ± 0.39 | 14.99 ± 0.77 |

The results show that the compositions of the present invention reach maximum mechanical property earlier and that maximum is greater than those for compositions having camphorquinone/organic amine alone as catalyst.

The mechanical properties were determined on a Howden Testing machine—Type EU 5 BS as follows:

1. Flexural Strength and Flexural Modulus. After immersion in deionised water for 24 hours (except Example 1) at 37° C., the samples were dried with tissue paper and allowed to equilibrate at room temperature for 10 minutes. Rough edges on samples were carefully sanded down using emery cloth grade 0. Cross-sectional dimensions were determined on each sample using a micrometer. Three point bend test was then carried out on each sample using a 200N load cell and a cross-head speed of 1.0±0.05 mm/minute. The load at failure was recorded and flexural strength (FS) calculated according to the following formula:

$$FS = \frac{3PL}{2bd^2} \, N/mm^2$$

where
P is the load at failure (N)
L is the distance between supports (mm correct to 0.01 mm)
b is breadth of sample (mm correct to 0.01 mm)
d is depth of sample (mm correct to 0.01 mm)

Flexural modulus (FM) was calculated according to the following formula:

$$FM = \frac{P^1 L^3}{4bd^3 y} \, GPa$$

where Lbd are defined above, y is the center point deflection (mm) of the beam on the testing machine and $P^1$ is the load on the linear portion of the load deflection corresponding to the deflection y.

2. Compressive strength. After immersion in deionised water for 24 hours (except Example 1) at 37° C., the samples were dried with tissue paper and allowed to equilibrate at room temperature for 10 minutes. The diameter was measured with a micrometer; each sample was mounted in the upright position between parallel plattens of the testing machine and tested under compression until failure. The load at failure (P measured in Newtons) was recorded and compressive strength (CS) calculated according to the formula:

$$CS = \frac{P}{\pi r^2}, \, N/mm^2$$

where r is the radius of sample cross-section (measured in mm correct to 0.01 mm).

3. Diametral tensile strength. After immersion in deionised water for 24 hours at 37° C., samples were dried with tissue paper and allowed to equilibrate at room temperature for 10 minutes. The length and diameter of each sample was measured using a micrometer. Each sample was placed on its side between parallel plattens of the testing machine and tested under compression of 1.0±0.05 mm/min; the load at failure (T measured in Newtons) was recorded and diametral tensile strength (TS) calculated according to the formula:

$$TS = \frac{2T}{\pi DL} \, N/mm^2$$

where D and L are the diameter and length respectively of the sample (measured in mm correct to 0.01 mm).

In evaluating each property above, the result from 12 samples was averaged, and any value which fell more than 15% below the average was discarded. The mean of the remaining samples was recorded with a standard deviation. The tests were repeated if more than 3 samples were discarded.

EXAMPLE 11

Two compositions (a and b) were prepared according to the procedure of Example 1 except that the catalyst content was as follows:

(a)

camphorquinone 0.5%
benzoyl peroxide 2.5%
'Topanol' OC 0.025%

(b)

camphorquinone 0.5%
t-butyl perbenzoate 2.4%
'Topanol' OC 0.025% in which the percentages of catalyst components are based on polymerisable material.

Samples of the initially fluid compositions were stored in the absence of light and air at ambient temperature. After 4 months, composition (a) had become much stiffer and ceased to be fluid, whereas viscosity characteristics of composition (b) were essentially unchanged after 12 months.

We claim:

1. A visible light cure fluid dental composition which comprises at least one polymerisable ethylenically unsaturated material, from 40% to 90% by weight of the composition of at least one particulate filler, and a catalyst which comprises camphorquinone and at least one organic peroxide.

2. A composition according to claim 1 in which the concentration of camphorquinone is from 0.01% to 2% by weight of polymerisable material.

3. A composition according to claim 1 in which the concentration of organic peroxide is from 0.1% to 20% by weight of polymerisable material.

4. A composition according to claim 1 in which the organic peroxide has a ten hour half life temperature of less than 150° C. and has the formula R—O—O—R in which the groups R which may be the same or different are hydrogen, alkyl, aryl or acyl groups, no more than one of the groups being hydrogen.

5. A composition according to claim 4 in which the organic peroxide is tertiary butyl perbenzoate.

6. A composition according to claim 1 which includes a reducing agent which is capable of reducing the camphorquinone when the latter is in an excited state.

7. A composition according to claim 6 in which the reducing agent is an organic amine which has the formula $R^4{}_3N$ where the groups $R^4$, which may be the same or different, are hydrogen atoms, hydrocarbyl groups, substituted hydrocarbyl groups or groups in which two units $R^4$ together with the nitrogen atom form a cyclic ring system, no more than two of the units $R^4$ being hydrogen atoms and where the nitrogen atom is attached directly to an $R^4$ group which is aromatic, at least one of the other units $R^4$ has a group attached to the nitrogen atom.

8. A method of curing a visible light cure fluid dental composition which comprises at least one polymerisable ethylenically unsaturated material, from 40% to 90% by weight of the composition of at least one particulate filler, and a catalyst which comprises camphorquinone, and at least one organic peroxide which comprises irradiating the composition with visible light having a wavelength in the range 400 mµ to 500 mµ.

9. A method according to claim 8 in which the concentration of camphorquinone is from 0.01% to 2% by weight of polymerisable material.

10. A method according to claim 8 in which the concentration of organic peroxide is from 0.1% to 20% by weight of polymerisable material.

11. A method according to claim 8 in which the organic peroxide has a ten hour half life temperature of less than 150° C. and has the formula R—O—O—R in which the groups R which may be the same or different are hydrogen, alkyl, aryl or acyl groups, no more than one of the groups being hydrogen.

12. A method according to claim 11 in which the organic peroxide is tertiary butyl perbenzoate.

13. A method according to claim 8 which includes a reducing agent which is capable of reducing the camphorquinone when the latter is in an excited state.

14. A method according to claim 13 in which the reducing agent is an organic amine which has a formula $R^4{}_3N$ where the groups $R^4$, which may be the same or different, are hydrogen atoms, hydrocarbyl groups, substituted hydrocarbyl groups or groups in which two units $R^4$ together with the nitrogen atom form a cyclic ring system, no more than two of the units $R^4$ being hydrogen atoms and where the nitrogen atom is attached directly to an $R^4$ group which is aromatic, at least one of the other units $R^4$ has a group attached to the nitrogen atom.

15. In a method of curing a visible light cure fluid dental composition which comprises at least one polymerisable ethylenically unsaturated material, from 40–90% by weight of the composition of at least one particulate filler, and a light sensitive catalyst, the improvements which comprise using as the catalyst camphorquinone, and at least one organic peroxide and irradiating the composition with visible light having a wave length in the range 400 mµ–500 mµ, whereby the composition has improved depth of cure.

* * * * *